United States Patent [19]
Sasaki

[11] Patent Number: 5,408,265
[45] Date of Patent: Apr. 18, 1995

[54] ELECTRONIC ENDOSCOPE SYSTEM ADAPTABLE TO DIFFERENT T.V. STANDARDS WHILE UTILIZING A COMMON LIGHT SOURCE

[75] Inventor: Masahiko Sasaki, Hachioji, Japan
[73] Assignee: Olympus Optical Co., Ltd., Tokyo, Japan
[21] Appl. No.: 9,870
[22] Filed: Jan. 26, 1993
[30] Foreign Application Priority Data
  Feb. 7, 1992 [JP] Japan ............... 4-022894
[51] Int. Cl.⁶ ............... H04N 7/18; A61B 1/04
[52] U.S. Cl. ............... 348/70; 348/71; 348/443
[58] Field of Search ............... 358/98, 140, 24, 69, 358/71; 348/70, 71, 69, 68, 65, 443, 441, 444, 454

[56] References Cited
U.S. PATENT DOCUMENTS

| | | | |
|---|---|---|---|
| 4,587,557 | 5/1986 | Doornheim | 358/140 |
| 4,891,701 | 1/1990 | Shikina et al. | 348/443 |
| 4,983,019 | 1/1991 | Ikuno et al. | 358/98 |
| 5,216,512 | 6/1993 | Bruijns et al. | |
| 5,221,966 | 6/1993 | Clayton et al. | 348/443 |
| 5,241,281 | 8/1993 | Wilkes et al. | 348/443 |
| 5,255,091 | 10/1993 | Lyon et al. | 348/443 |
| 5,309,224 | 5/1994 | Usuki et al. | 348/443 |

Primary Examiner—Tommy Chin
Assistant Examiner—Bryan S. Tung
Attorney, Agent, or Firm—Armstrong, Westerman, Hattori, McLeland & Naughton

[57] ABSTRACT

In an electronic endoscope system, an imaging device images a subject at a first frame frequency. A signal generating unit receives image signals of the subject imaged by the imaging device to generate signals of a standard TV system having a second frame frequency that is approximately n/m-fold (where, n and m are natural numbers, and n is unequal to m) of the first frame frequency. Then, a timing control unit synchronizes the first frame frequency of the imaging device with the second frame frequency using a predetermined timing signal output by the signal generating unit. The timing controller can also synchronize a first frame frequency of a color field sequential illumination unit with a second frame frequency using a predetermined timing signal.

16 Claims, 12 Drawing Sheets

ELECTRONIC ENDOSCOPE SYSTEM ADAPTABLE TO DIFFERENT T.V. STANDARDS WHILE UTILIZING A COMMON LIGHT SOURCE

BACKGROUND OF THE INVENTION

1. Field of the Invention

The present invention relates to a color field sequential imaging type electronic endoscope system. More particularly, this invention is concerned with a construction for enabling common use of a light source apparatus for color field sequential illumination irrelevant of a standard television (TV) system of, for example, a display unit.

2. Description of the Related Art

An endoscope, an elongated insertion section of which can be inserted into a body cavity to observe an organ or the like in the cavity or, if necessary, a treatment adaptor inserted through a treatment adaptor channel thereof can be used to conduct various treatments, has been widely utilized in recent years. Such an endoscope is utilized not only in medicine but also in the field of industry.

A variety of electronic endoscopes using charge coupled devices (CCD) or other solid state imaging devices have been proposed and are being put to practical use.

For an endoscope, the diameter of an insertion section must be made small. This restricts the size of a solid state imaging device, making it difficult to increase resolution. In a field sequential method, rays of illumination light with different wavelengths are emitted sequentially via a color rotary filter, and respective color image signals acquired under respective illumination light are synthesized to produce a color image. The field sequential method has the following advantage: the field sequential mode can provide color images with higher resolution than a simultaneous method in which color imaging is performed under white illumination light using an imaging means with color filters.

An example of the foregoing electronic endoscope system of field sequential imaging type has been disclosed in Japanese Patent Laid-Open No.61-82731. A light source apparatus for this electronic endoscope system requires a color rotary filter for sequentially switching white illumination light into red (R), green (G), and blue (B).

On the other hand, a signal processing unit for converting imaging signals acquired by the foregoing field sequential type imaging device into standard TV signals is available in different color television (TV) systems; such as, a system of phase alternation by line (PAL), a system recommended by National Television System Committee (NTSC), and a séquential couleur á mémoire (SECAM) system. Accordingly, there exist monitors for these respective systems.

Furthermore, for a light source apparatus, for example, the areas of R, G, and B transmission windows of a rotary filter differ among the foregoing TV systems. The rotational frequency of the rotary filter also differs among the forgoing TV systems. That is to say, control of the rotating speed or the like of the filter differs with the TV system.

Therefore, when an endoscope system has a video processor or monitor of different video or television systems such as PAL and NTSC, light sources for controlling the rotary filter associated with different TV systems such as PAL and NTSC are required, as described above. In other words, multiple kinds of light source apparatuses must be installed.

The present applicant has proposed a light source apparatus for solving the aforesaid problem in Japanese Patent Laid-Open No.1-217413. In this light source apparatus, a rotary color filter for generating color field sequential light rays, formed like a cassette, is detachably provided. In the light source apparatus, the controlled speed of a rotary filter is changed according to the type of an inserted filter cassette.

With the light source apparatus, by changing a rotary color filter cassette and selecting multiple kinds of built-in synchronizing signal generating circuits, this single light source apparatus can cope with multiple TV systems.

Japanese Patent Laid-Open No.3-68330 has proposed a light source apparatus in which rotating speed of a rotary filter and a phasing mode can be changed according to the type of a main unit used in combination with the light source apparatus. According to the electronic endoscope system in this reference, the rotational frequency of the rotary color filter can be changed and servo control with high precision can be achieved. The light source apparatus can also cope with multiple TV systems by varying rotational frequency of the rotary color filter.

As described above, a field sequential type electronic endoscope system employs a color field sequential illumination light source apparatus having a repetition period that is dependent on a TV system of a display unit, because the frame frequency of an image signal differs with the TV system of a display unit. The NTSC system, for example, employs a light source apparatus that emits RGB illumination light at a repetition period of 29.97 Hz, while the PAL system employs a light source apparatus having a repetition period of 25 Hz. In these systems, imaging in each of R, G, B colors is completed in units of a one-frame period of display. Therefore, writing or reading in or from memories, which is intended to synchronize color field sequential signals, can be controlled easily. However, since the aforesaid conventional light source apparatus includes multiple servo circuits internally, the circuitry becomes large in size and complex, and the number of control processes increases. This is a primary reason for a high cost.

Alternatively, different video processors are installed depending on multiple TV systems of a monitor and a recording unit, as described above. Consequently, light sources must be developed independently for the processors. This deteriorates development efficiency. Moreover, mass production effect cannot be expected because a light source apparatus cannot be used in common.

SUMMARY OF THE INVENTION

An object of the present invention is to provide an electronic endoscope system that outputs signals conformable to different TV systems and that offers an increased number of common circuits to reduce costs and to improve development efficiency.

Another object of the present invention is to provide an electronic endoscope system capable of easily generating a TV signal, which has a different frame frequency from an imaging or illuminating system, without causing out of synchronism or lead scan.

Yet another object of the present invention is to provide an electronic endoscope system which enables color field sequential imaging using a common color field sequential light source apparatus even when the TV system differs between a display unit or a recording unit and an illuminating or imaging system in an endoscope or a light source apparatus.

Yet another object of the present invention is to provide an electronic endoscope system that enables use of a common color field sequential illuminating means even when the TV system differs among units and that permits improved system development efficiency and reduced costs.

Yet another object of the present invention is to provide an electronic endoscope system that can phase a synchronizing signal or a timing signal for signal processing irrespective of a difference in the TV system when the TV system differs between units or between circuits.

Yet another object of the present invention is to provide an electronic endoscope system that enables stable phasing of a synchronizing signal or a timing signal for signal processing irrespective of a difference in the TV system even during unstable operation after a power supply is turned on, when the TV system differs between units or between circuits.

Yet another object of the present invention is to provide an electronic endoscope system capable of phasing a synchronizing signal or a control signal for signal processing on a stable basis, unaffected with a jitter of a rotary filter in an illuminating system when the TV system differs between a display unit or a recording unit and an illuminating or imaging system.

In a preferred embodiment, an electronic endoscope system of this invention includes an imaging means for imaging a subject at a first frame frequency, a signal generating means that receives image signals of the subject imaged by the imaging means and generates signals of a standard TV system having a second frame frequency which is approximately n/m-fold (where, n and m are natural numbers, and n is unequal to m) of the first frame frequency, and a timing control means for synchronizing the first frame frequency of the imaging means with the second frame frequency using a predetermined timing signal output from the signal generating means.

In another preferred embodiment, an electronic endoscope system of the present invention includes a color field sequential illuminating means that emits color field sequential illumination light for sequentially illuminating a subject with multiple light rays of different color components at a first frame frequency, a signal generating means which receives image signals acquired under the illumination light of the color field sequential illuminating means and generates signals of a standard TV system having a second frame frequency which is approximately n/m-fold (where, n and m are natural numbers, and n is unequal to m) of the first frame frequency, and a timing control means for synchronizing the first frame frequency of the color field sequential illuminating means with the second frame frequency using a predetermined timing signal the signal generating means outputs.

According to an electronic endoscope system of the present invention in yet another preferred embodiment, a color field sequential illuminating means emits color field sequential illumination light for sequentially illuminating a subject with multiple light rays of different color components at a frame frequency of a first standard TV signal. An imaging means images the subject under illumination light from the color field sequential illuminating means. A signal generating means uses the color field sequential image signals acquired by the imaging means to generate video signals of a second standard TV system having a frame frequency which is approximately n/m-fold (where, n and m are natural numbers, and n is unequal to m) of that of the first standard TV system. Furthermore, according to the electronic endoscope system of the present invention, a first control means generates a pseudo imaging sync signal having a frame frequency that is approximately m/n-fold of that of the second standard TV system in order to control the color field sequential illuminating means, and controls the imaging means so that color field sequential imaging will be done at a frame frequency which is m/n-fold of that of the second standard TV system. A second control means generates a synchronizing signal of the second standard TV system. A detecting means detects at least either a repetition period or a phase of the color field sequential illuminating means. A timing control means compares at least either the period or phase detected by the detecting means with the synchronizing signal provided by the second control means, and phases a signal input from the first control means, based on the comparison result. A color field sequential illumination control means controls the phase of color field sequential illumination repeated in the color field sequential illuminating means so as to be synchronized with the pseudo imaging sync signal input by the first control means.

The other features and advantages of the present invention will be apparent from the detailed description below.

BRIEF DESCRIPTION OF THE DRAWINGS

FIG. 6 is an explanatory view showing a change in the rotating speed of a motor after a power supply is turned on;

DETAILED DESCRIPTION OF THE PREFERRED EMBODIMENTS

Figure 1:
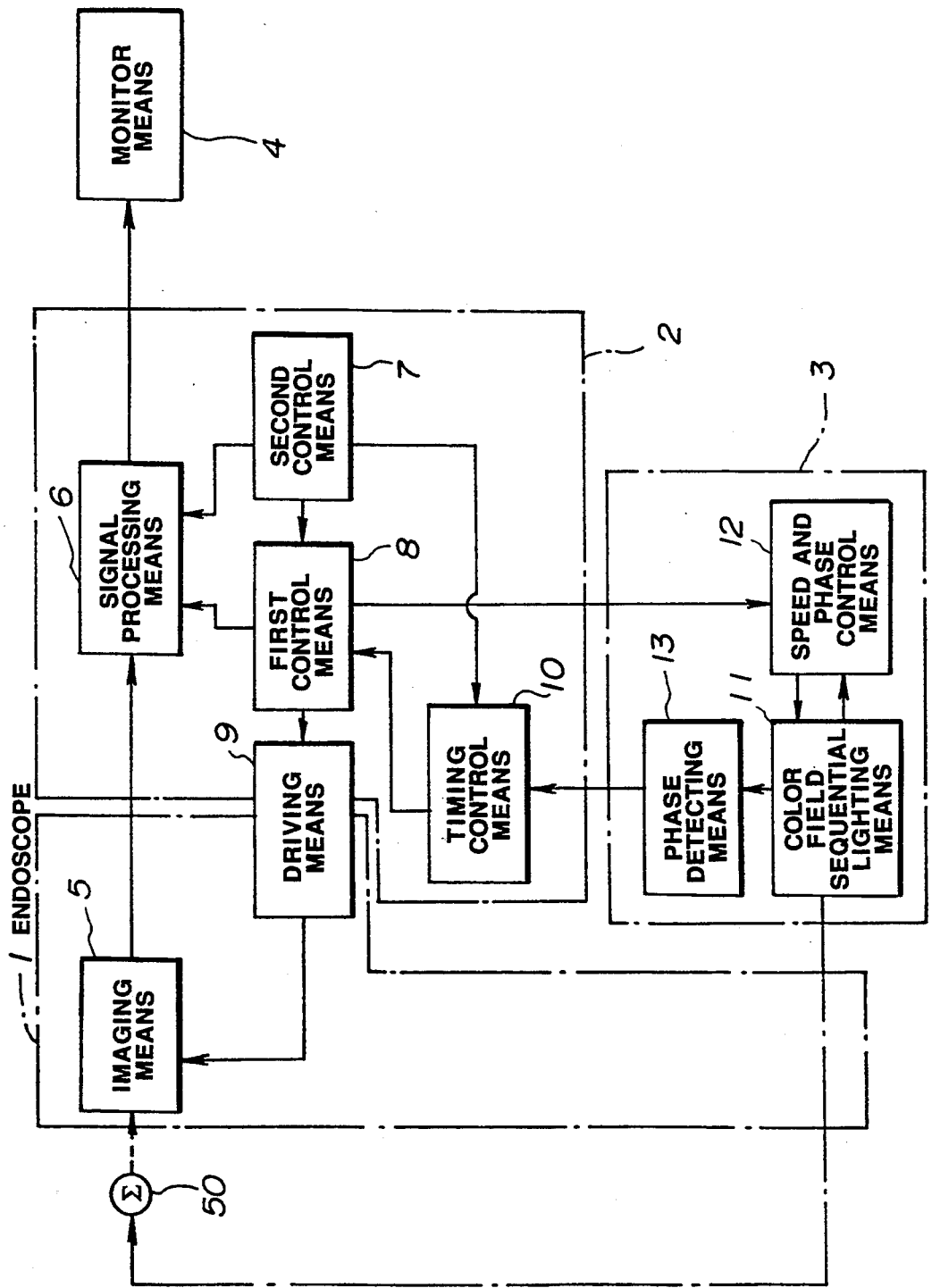
FIG. 1 is a conceptual diagram of the present invention.

An electronic endoscope system of the present invention will be outlined on the basis of an example of a construction shown in FIG. 1 or a conceptual diagram of the present invention.

An electronic endoscope system shown in FIG. 1 comprises an endoscope 1 including an imaging means for imaging a subject 50 and outputting signals, a signal processing unit 2 including a signal processing means 6 for converting output signals of the imaging means 5 into first standard TV signals, a light source apparatus 3 for generating color field sequential illumination light, detecting a repetition period and a phase of illumination light, and outputting the detected repetition period and phase to the signal processing unit, and a monitor means 4 for displaying a signal sent from the signal processing means 6.

The signal processing unit 2 includes a second control means 7 for generating a synchronizing signal of a second standard TV system, a first control means 8 that uses the synchronizing signal of the second standard TV system sent from the second control means 7 to generate an imaging sync signal and a pseudo imaging sync signal of a first standard TV system, a driving means 9 that uses the imaging sync signal to generate and output a drive signal for driving the imaging means 5, and a timing control means 10 for comparing a phase detected by a phase detecting means, which will be described later, with the synchronizing signal sent from the second control means, and matching the initial phases of the imaging sync signal and pseudo imaging sync signal generated by the first control means 8 on the basis of the comparison result.

Herein, the second standard TV system has a frame frequency that is approximately n/m-fold (where, n and m are natural numbers, and m is unequal to n) of that of the first standard TV system.

The first control means 8 sets a repetition period that is m/n-fold of the frame frequency of the second standard TV system in response to the synchronizing signal of the second standard TV system, generates an imaging sync signal of the first standard TV system, and outputs the imaging signal sync signal to the driving means 9 and to signal processing means 6. At the same time, the first control means 8 generates a pseudo imaging sync signal whose frame frequency is approximately m/n-fold of that of the second standard TV system and outputs the pseudo imaging sync signal to the light source apparatus 3.

The timing control means 10 compares the synchronizing signal of the second standard TV system sent from the second control means 7 with a phase signal provided by a phase detecting means 13 of the light source apparatus 3, and resets the first control means 8 on the basis of the comparison result.

The signal processing means 6 is under the control of the imaging sync signal sent from the first control means before it synchronizes color field sequential image signals sent from the imaging means 5. After completing synchronization of the color field sequential image signals, the signal processing means 6 is under the control of the synchronizing signal sent from the second control means 7 until it outputs the synchronized color field sequential image signals to the display means 4.

The light source apparatus 3 includes a color field sequential illuminating means 11 for generating color field sequential illumination light, a speed/phase control means 12 serving as a color field sequential illumination control means for controlling the repetition period of illumination light in response to the pseudo imaging sync signal provided by the first control means 8, and a phase detecting means 13 for detecting a phase of repetition of color field sequential illumination light.

In the aforesaid construction, the speed/phase control means 12 of the light source apparatus 3 receives an input from the signal processing unit 2, and controls the repetition period of the color field sequential illuminating means 11 in response to a pseudo imaging sync signal indicating the timing of imaging. The phase detecting means 13 detects a cyclic phase of the color field sequential illuminating means 11, and outputs the detected signal to the timing control means 10 of the signal processing unit 2.

An optical image of a subject produced under color field sequential illumination light irradiated by the light source apparatus 3 is formed on the imaging plane of the imaging means 5 located at the distal end of the endoscope 1.

The imaging means 5 is driven for imaging by the first control means 8 in a cycle of a frame frequency that is m/n-fold (where, m and n are natural numbers) of the frame frequency of the second standard TV system, and provides the signal processing means 6 with image signals acquired on a color field sequential basis.

The signal processing means 6 performs given signal processing; such as, clamping, AGC, white balance control, and gamma correction on the provided color field sequential image signals, then converts the signals into digital signals. Thereafter, the signal processing means 6 synchronizes the color field sequential signals using memory means which are not shown. The operations, which are performed after the color field sequential image signals are input and subjected to various signal processing until the processed color field sequential image signals are written in the memory means and synchronized, are performed in response to the imaging sync signal by the first control means. The imaging sync signal is conformable to the first standard TV system.

The field sequential image signals stored in the memory means are read simultaneously in response to the synchronizing signal of the second standard TV system by the second control means 7. The read color signals are subjected to various signal processing, fed to the monitor means 4 together with the synchronizing signal of the second standard TV system, then displayed as an endoscopic image.

As described above, in the field sequential type electronic endoscope system, a monitor means, an endoscope, and a light source apparatus can be used in combination for observation, although the TV system differs between the illuminating and imaging methods thereof.

According to a field sequential type electronic endoscope system shown in FIG. 1, a means for compensating for an error between the repetition periods of a field sequential imaging means and of a color field sequential illuminating means is installed on a signal processing unit. Therefore, the color field sequential illuminating means can be used in common irrelevant of the TV system. This helps improve system development efficiency and reduce costs.

Figure 2:
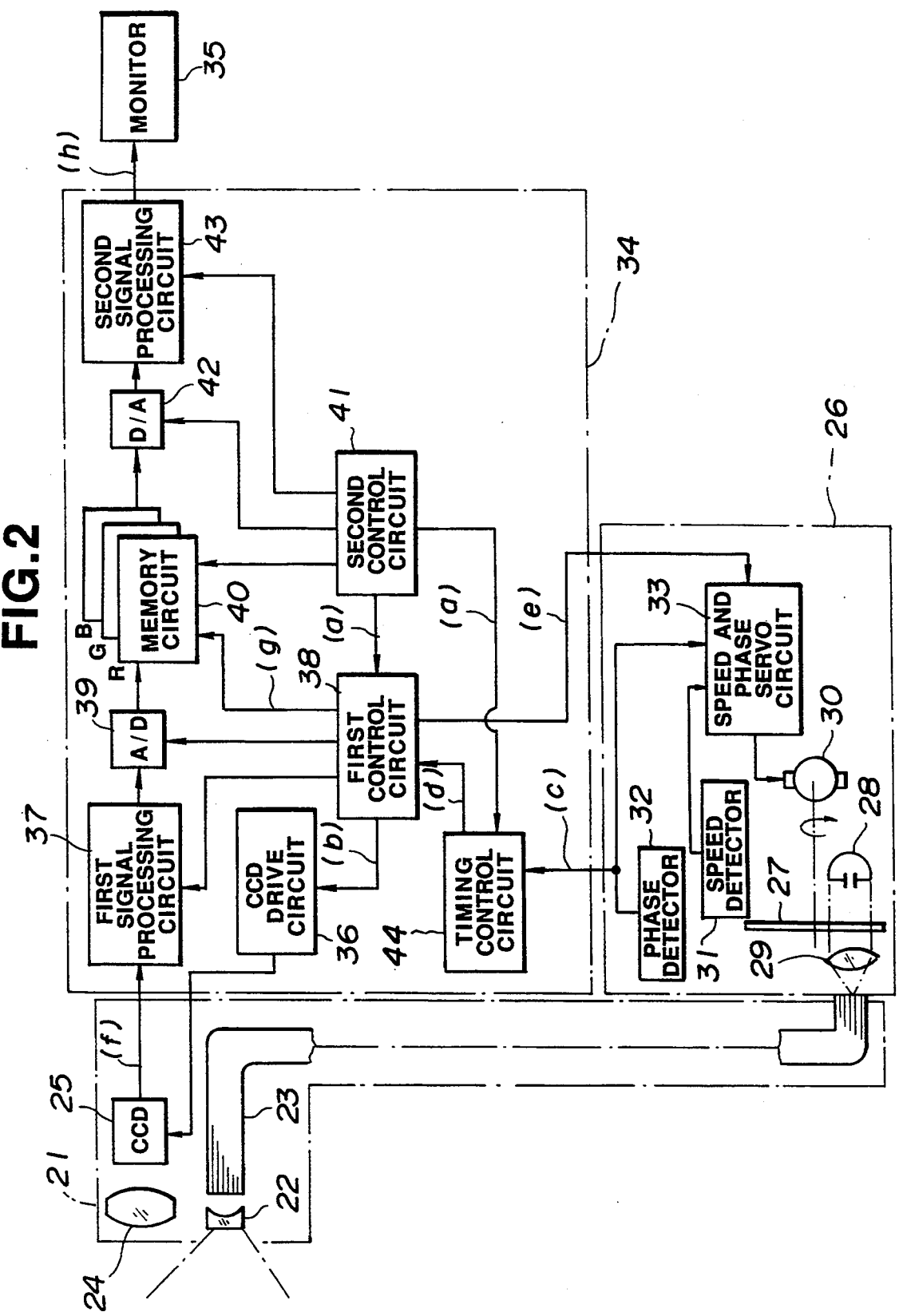
FIG. 2 is a block diagram of an electronic endoscope system relating to the first embodiment.

FIG. 2 shows the first embodiment of the present invention. This embodiment will be described using an example in which imaging is done under color field sequential illumination light conformable to, for example, the NTSC system that is regarded as a first standard TV system, and color field sequential image signals are displayed on a monitor means of, for example, the PAL system that is regarded as a second standard TV system.

In an endoscope 21, a light distribution lens 22 is arranged at the distal end of an insertion section, and an emission end of a light guide 23 is located on the proximal side of the light distribution lens 22. The incident end of the light guide 23 receives rays of color illumination light sequentially from a light source apparatus 26. In the endoscope 21, an objective optical system 24 is also arranged at the distal end of the insertion section, and a CCD 25 serving as an imaging means is located on the proximal side of the objective optical system 24. The CCD 25 forms an image of a subject illuminated with color field sequential illumination light on its imaging plane thereof, then outputs image signals produced by photoelectric conversion to a signal processing unit 34.

The light source apparatus 26 has a construction described below as a color field sequential illuminating means. Specifically, the light source apparatus 26 comprises a rotary color filter 27 in which three optical color filters of red, green, and blue are arranged at equal intervals on a circumference, a lamp 28 for generating while light, a lens 29 for converging illumination light on a single surface of the light guide, and a motor 30 for rotating the rotary color filter. The light source apparatus 26 further includes a speed detector 31 for detecting a rotating speed of the rotary color filter 27, a phase detector 32 for detecting a phase of the rotary color filter 27, and a speed/phase servo circuit 33 serving as a color field sequential illumination control means for controlling the rotation of the motor 30 according to the results of detecting the speed and phase in response to a pseudo imaging sync signal sent from a signal processing circuit which will be described later.

The speed detector 31 is realized with, for example, a frequency oscillator installed in the motor 30 and outputs pulses c by the number of revolutions of the motor. The phase detector 32 is realized with, for example, a photosensor and detects a rotational phase of the rotary color filter 27 by detecting reflected light of a reflector, which is not shown, located at a given position on, for example, the rotary color filter 27.

In the color field sequential illuminating means, as the rotary color filter 27 rotates, an exposure time during which light passes and an interception time during which light is intercepted are established. The signal processing unit 34 reads charges, which are accumulated in the CCD 25 during the exposure time, during the interception time, and acquires color field sequential image signals. Therefore, transmission of image signals must be synchronized with rotation of the rotary color filter 27. The speed/phase servo circuit 33 controls the rotation of the rotary color filter 27 by performing phase synchronization control that includes speed control.

Assuming that the first standard TV system is NTSC, and the second standard TV system is PAL, operation will be described below.

In this embodiment, a rotary color filter 27 is set to rotate at a frame frequency of 19.98 Hz that is 3/2-fold of the NTSC frame frequency. The repetition period for color frames of red (R), green (G), and blue (B) amounts to 59.94 Hz. This means that color frames of color field sequential illumination are switched in unit of one NTSC field. The timing that a PAL field, a NTSC field, and a color frame of color field sequential illumination substantially agree with one another is used as the timing of phasing.

Color field sequential illumination light emitted by a light source apparatus 3 enters the incident end of a light guide 23 of an endoscope 21, passes through an emission end of the light guide 23 and a light distribution lens 22, then irradiates a subject. An optical image of the subject illuminated by color field sequential illumination is formed on an imaging plane of a CCD 25 via an objective lens 24 located at the distal end of the endoscope.

A signal processing unit 34 performs various processing on the color field sequential image signals f of the subject the CCD 25 outputs after imaging the subject under color field sequential illumination light, converts the signals into PAL TV signals, then outputs the PAL TV signals to a monitor 35. The monitor 35 inputs the PAL TV signals and displays a subject image.

The CCD 25 is driven by a CCD drive circuit 36 of a signal processing unit 34. Color field sequential image signals are read from the CCD 25 at a frame frequency that is 12/5-fold of the PAL frame frequency or at a repetition period of 60 Hz, then supplied to a first signal processing circuit 37.

The first signal processing circuit 37 performs various signal processing; such as, correlative double sampling (CDS), AGC, white balance control, painting, clamping, clipping, and gamma correction on the color field sequential image signals originating from the CCD 25 under the control of a first control circuit 38. The signals that have undergone the various processing are fed to memory circuits 40 via A/D converters 39.

The memory circuits 40 are in one-to-one correspondence to the colors of the color field sequential image signals originating from the CCD 25. Under the control of the first control circuit 38, color image signals R, G, and B are written in the associated memory circuits 40. Under the control of a second control means 41, the color signals are read simultaneously from the memory circuits 40 in response to the PAL TV signals. The read color signals pass through D/A converters 42 and enter a second signal processing circuit 43.

The second signal processing circuit 43 performs various signal processing on respective color image signals that have been made concurrent with one another synchronously with the PAL TV signals. The various signal processing include, for example, correction of irregular signal levels of color signals and correction of colors using matrix circuits which are not shown. After completing the various processing, the second signal processing circuit 43 outputs PAL TV signals (h) to the monitor 35. Alternatively, the second signal processing circuit 43 encodes the PAL TV signals, then outputs the encoded signals to the monitor 35.

The second control circuit 41 generates a standard (for example, PAL) TV synchronizing signal to control reading from the memory circuits 40, and operations of the D/A converters 39 and the second signal processing circuit 43. The second control circuit 41 outputs a PAL synchronizing signal PAL-$V_D$ to the first control circuit 38 and timing control circuit 44.

The first control circuit 38 uses the PAL synchronizing signal sent from the second control means 41 to generate a field sequential imaging sync signal (b) with a repetition period that is 12/5-fold of the PAL frame frequency, and outputs the signal (b) to a CCD drive circuit 36. At the same time, the first control circuit 38 uses the control signal generated using the synchronizing signal to control the operations of the first signal processing circuit 37 and A/D converters 39, and writing in the memory circuits 40 based on.

The first control circuit 38 generates a pseudo imaging sync signal (e) with a repetition period of 59.94 Hz that is 12/5-fold of the PAL frame frequency, and outputs the signal e to a speed/phase servo circuit 33 that controls a motor 30. The phases of the field sequential imaging sync signal b and pseudo imaging sync signal (e) are determined with a reset signal fed by the timing control circuit 44.

The timing control circuit 44 compares the PAL TV synchronizing signal (a) fed by the second control circuit 41 with a phase detecting signal (c) fed by a phase detector 32 of a light source apparatus 26, and resets the first control circuit 38 on the basis of the comparison result.

Figure 3:
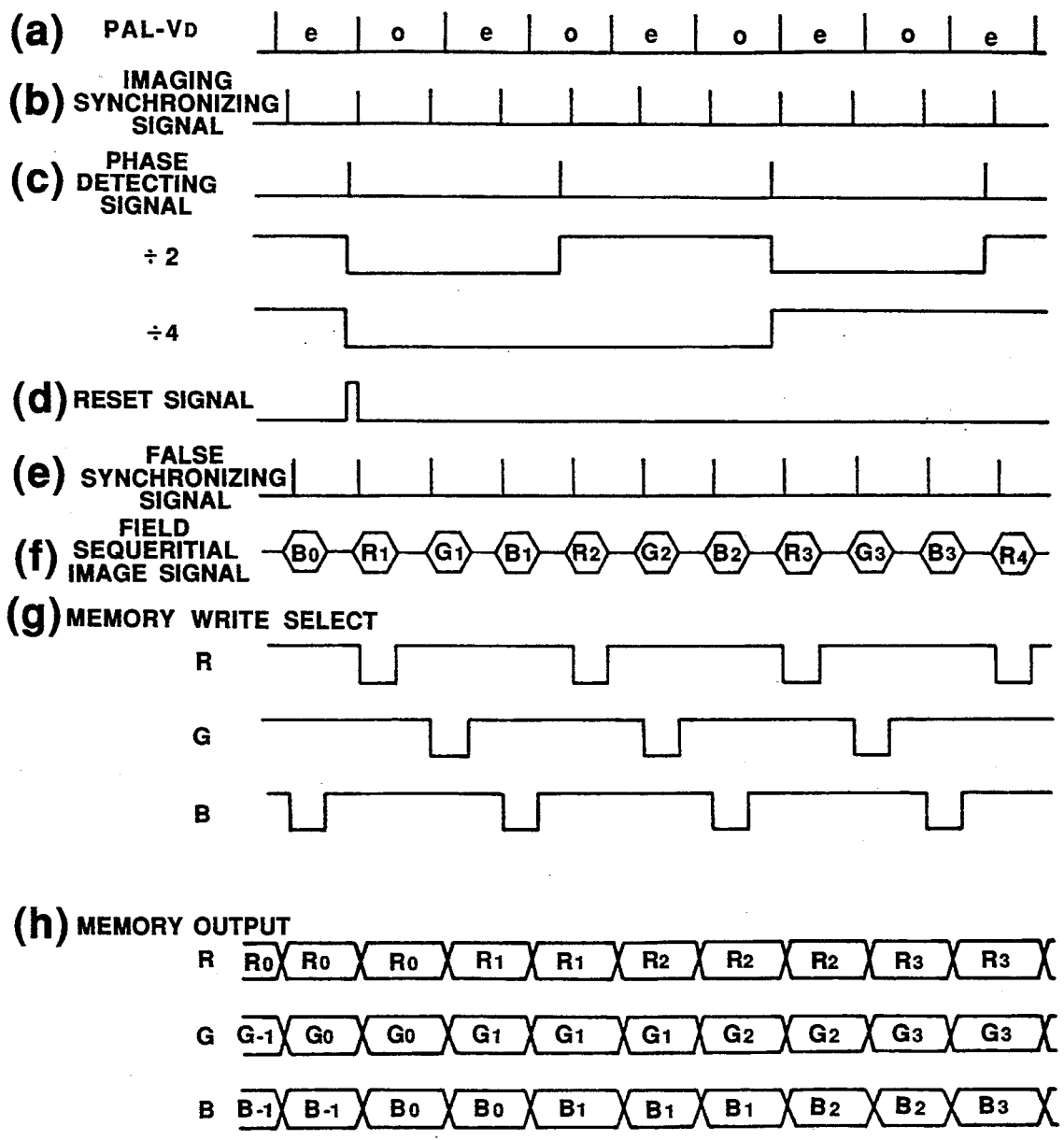
FIG. 3 shows waveforms of some of the signals in the system shown in FIG. 2.

FIG. 3 shows waveforms of some of the signals provided by the circuits shown in FIG. 2. A waveform (a) shown in FIG. 3 represents a PAL vertical synchronizing signal $V_D$ generated by a second control means 41. "e" and "o" in FIG. 3 denote even and odd fields. A waveform (b) represents a field sequential imaging sync signal generated by a first control circuit 38, which has a repetition period of 60 Hz. A waveform c represents an output of a phase detector 32, which is generated at the rate of one pulse per a rotation of a rotary color filter 27 immediately before red (R) illumination is completed.

A waveform (d) shown in FIG. 3 represents a reset signal generated by a timing control circuit 44. The reset signal d is generated when the phase of the PAL vertical synchronizing signal $V_D$ a for the initial odd field and that of the phase detecting signal (c) become a given value. The reset signal d will not lag or lead when generated using a quadruplex signal ($\div 4$) of the phase detecting signal (c). A duplex signal ($\div 2$) of the phase detecting signal (c) is an intermediate signal used to generate the quadruplex signal ($\div 4$). The reset signal is fed to the first control circuit 38, and initializes the control signals including the field sequential imaging sync signal b, pseudo imaging sync signal e, and memory write select signal g so that the control signals will have given phases. In short, the reset signal is a signal for performing phasing.

R, G, and B image data are read simultaneously from memory circuits 40 in response to a PAL TV synchronizing signal under the control of a second control means 41. On the other hand, since the image data in the memory circuits 40 are sequentially updated with input of field sequential image signals f, writing is controlled so as not to outpace reading, or vice versa.

According to the above construction, a common light source apparatus can be shared between a PAL electronic endoscope system and an NTSC electronic endoscope system.

In this embodiment, a means for compensating for an error between the repetition periods of a field sequential imaging means and a color field sequential illuminating means is installed on a signal processing means in a field sequential imaging type electronic endoscope system. Specifically, in this embodiment, a synchronizing signal generated by a first control circuit can be put in phase with a synchronizing signal of a second standard TV system by means of a timing control circuit. A common color field sequential illuminating means can be shared between different TV systems. This helps improve system development efficiency and reduce costs.

According to the present invention, the first standard TV system may be PAL and the second standard TV system may be NTSC, which is reverse to those in the first embodiment. The TV system is not limited to PAL and NTSC. Either of first and second standard TV systems may be SECAM. The present invention is not restricted to the aforesaid color television systems.

Figure 4:
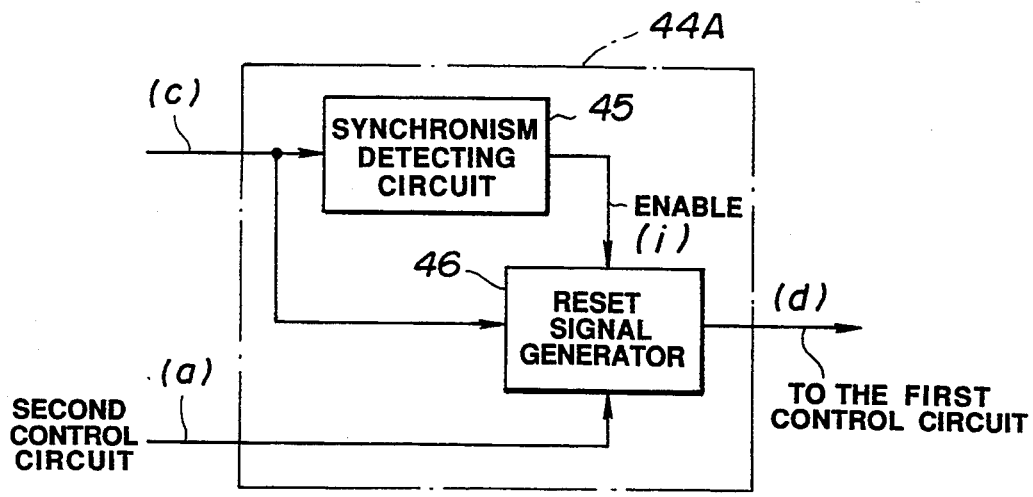
FIG. 4 is a block diagram of a timing control circuit.

FIG. 4 shows the second embodiment of the present invention.

The second embodiment includes a timing control circuit 44A instead of a timing control circuit 44 for the first embodiment shown in FIG. 2. The timing control circuit 44A can operate stably even in a transient state after a power supply is turned on. The other components identical to those of the first embodiment are assigned the same numerals. The components and the operation identical to that of the first embodiment will not be described.

Figure 5:
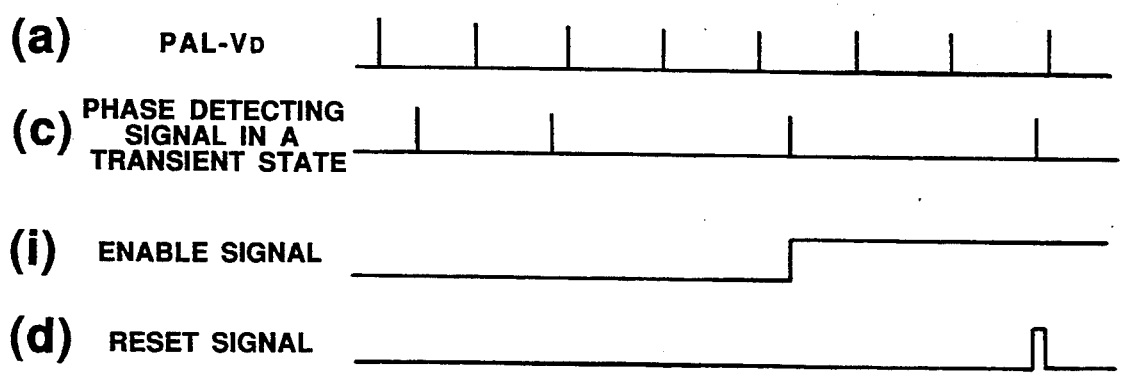
FIG. 5 shows waveforms of the signals in the circuits shown in FIG. 4 relating to the second embodiment.
Figure 6:
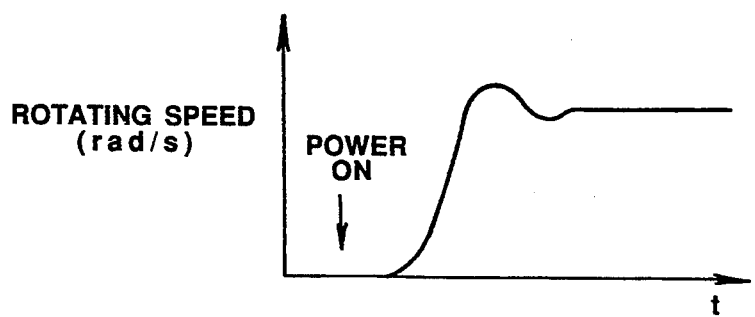

In a transient state, the rotating speed of a rotary filter 27 shows the responsiveness shown in FIG. 6. There is a possibility that a phase difference which will not occur normally may occur as shown in FIG. 5 between a PAL-VD signal (a) and a phase detecting signal (c). In this case, a color field sequential illuminating means and a CCD 25 cannot be synchronized, so that an image is disturbed. This embodiment has an innovative construction, whereby initialization of phases will be unstable in a transient state after a power supply is turned on.

A timing control circuit 44A comprises a period detector 45 and a reset signal generating circuit 46.

The period detector 45 continuously detects a repetition period of a phase detected signal (c) fed by a phase detector 32 of a light source apparatus 3. When the period indicates a given width, the period detector 45 Outputs an enable signal (i) to the reset signal generating circuit 46, and thus enables the reset signal generating circuit 46 to output a reset signal. At this time, the reset signal generating circuit 46 operates in the same manner as a timing control circuit 44 described in the first embodiment. The description will, therefore, be omitted. The reset signal generating circuit 46 does not output a reset signal unless permitted.

Owing to the above construction, unstableness in the operation of the timing control circuit 44A occurring in a transient state can be alleviated. The other components, and the operation and advantages are identical to those of the first embodiment. The description will, therefore, be omitted.

Figure 7:
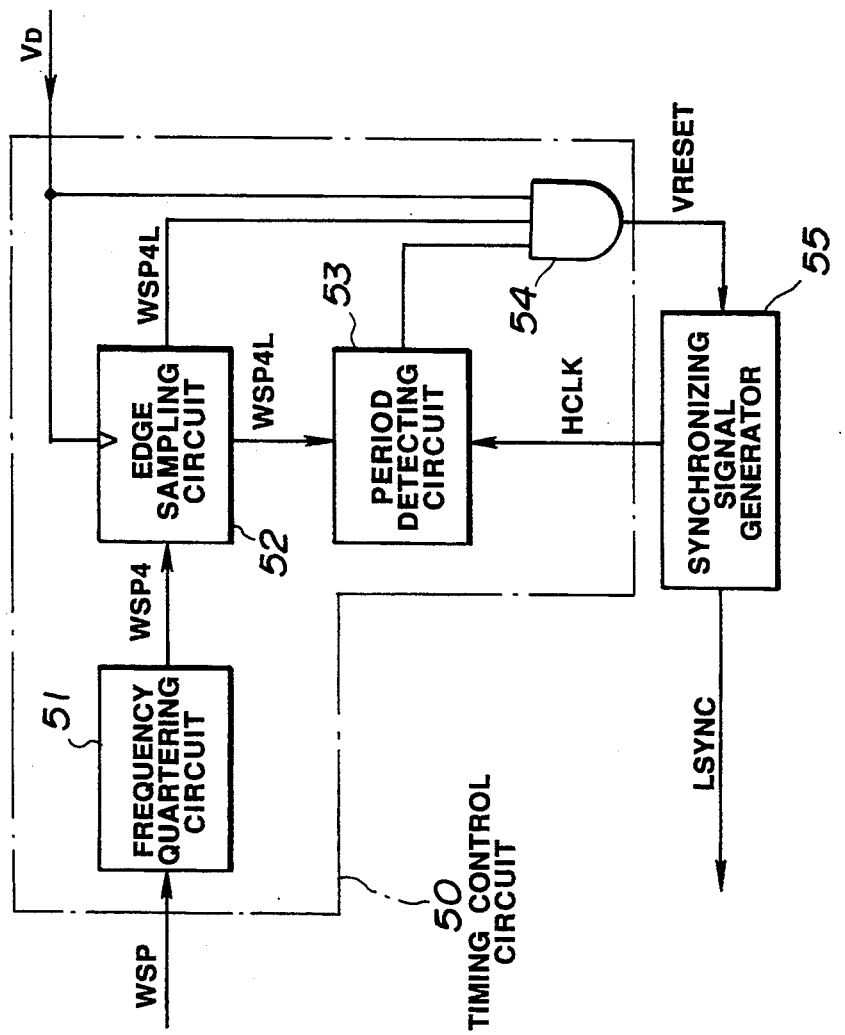
FIG. 7 is a block diagram of a timing control circuit relating to the third embodiment.
Figure 8:
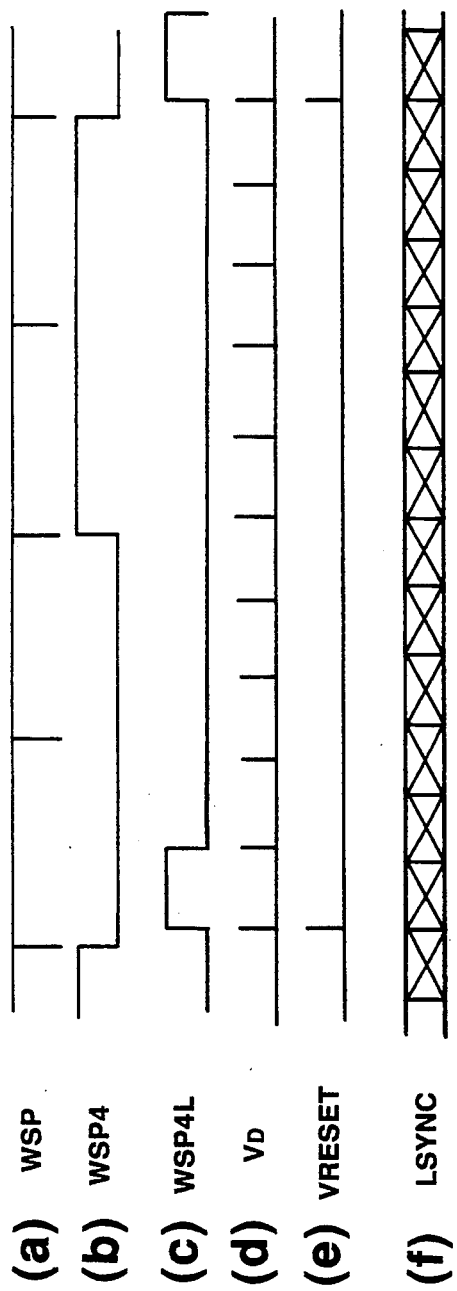
FIG. 8 shows waveforms of the signals in the circuits shown in FIG. 7.

FIGS. 7 and 8 relate to the third embodiment of the present invention. FIG. 7 is a block diagram showing an example of a timing control circuit. FIG. 8 shows waveforms representing the operations of the circuits shown in FIG. 7.

A timing control circuit 50 in the third embodiment shown in FIG. 7 has a frequency quartering circuit 51 serving as a frequency dividing means that inputs a phase detected signal WSP provided by a phase detector 32 shown in FIG. 2. The timing control circuit 50 further includes an edge sampling circuit 52 serving as an edge sampling means that outputs a synchronous period signal, a period detector 53 serving as a specified period detecting means, and an AND gate 54 having three inputs and serving as a gate means.

An output of the AND gate 54 is fed to a synchronizing signal generating circuit 55 serving as a first control means. The synchronizing signal generating circuit 55 outputs a horizontal synchronizing signal CLK to the period detector 53.

The frequency quartering circuit 51 quarters the frequency of the phase detecting signal WSP. The edge sampling circuit 52 generates a signal representing a sampled edge of a quartered phase detected signal WSP4 the frequency quartering circuit 51 outputs. At the trailing edge of the received quartered phase detected signal WSP4, the edge sampling circuit 52 outputs a quartered phase edge sampled signal WSP4L (hereafter, abbreviated as WSP4L signal) that is synchronized with a vertical synchronizing signal $V_D$ output by a second control circuit 41. The WSP4L signal is a synchronous period signal, which is, for example, high in a period of time from a PAL vertical synchronizing signal $V_D$ following the trailing edge of the quartered phase detected signal WSP4 to the next vertical synchronizing signal $V_D$.

The period detector 53 detects whether or not the period of the WSP4L signal is within a specified period, using a horizontal synchronizing signal HCLK sent from the synchronizing signal generating circuit 55 as a reference.

The AND gate 54 provides the AND of the vertical synchronizing signal $V_D$, the WSP4L signal, and an output of the period detector 53. Then, when these three signals are high, the AND gate 54 outputs a reset signal VRESET for phasing a pseudo imaging sync signal LSYN generated by the synchronizing signal generating circuit 55.

In the foregoing construction, the frequency quartering circuit 51 quarters the phase detected signal WSP (See FIG. 8a) representing a cycle of a color field sequential illuminating means, and provides the quartered phase detected signal WSP4 shown in FIG. 8b. Then, the edge sampling circuit 52 samples one vertical period (vertical scanning line interval) immediately after the trailing edge of the WSP4 signal, and outputs the WSP4L signal shown in FIG. 8c. FIG. 8d shows a PAL vertical synchronizing signal $V_D$.

The period detector 53 checks whether the vertical period of the WSP4L signal is within a predetermined width. If the vertical period is within the predetermined width, a high-level signal is supplied.

The PAL vertical synchronizing signal $V_D$, the WSP4L signal, and the output of the period detector 53 are ANDed by the AND gate 54, providing a reset signal VRESET shown in FIG. 8e. The reset signal VRESET is used to reset the synchronizing signal generating circuit 55, or for phasing.

As described above, in this embodiment, since a signal width is predetermined, after the power supply is turned on, phasing is carried out when the period of the phase detected signal WSP changes from an unstable state to a steady state.

The synchronizing signal generating circuit 55 generates a pseudo imaging sync signal LSYNC shown in FIG. 8f. The phase of the pseudo imaging sync signal LSYNC is locked onto a vertical repetition period with a predetermined timing signal (VRESET signal). Then, the synchronizing signal generating circuit 55 sends the pseudo imaging sync signal LSYNC to a speed/phase servo control circuit 33, which is shown in FIG. 1, serving as a color field sequential illumination control means.

Assuming that the first standard TV system is NTSC and the second standard TV system is PAL, since the foregoing vertical period is allocated to the PAL system, the vertical period measures 20 msec. The pseudo imaging sync signal LSYNC corresponds to an NTSC composite synchronizing signal whose phase error is reset at every 12 vertical scanning line intervals for a PAL vertical period.

When the synchronizing signal generating circuit 55 is reset using the edge of the WSP4 signal as it is, a feedback system is formed between a servo system of a color field sequential illuminating means, and a timing control circuit or a synchronizing signal generating circuit 55. The WSP signal represents a detected rotational phase of a rotary filter 27, which, therefore, contains a jitter component. The WSP4 signal obtained by quartering the WSP signal also contains a jitter component. Therefore, the construction which uses the edge of the WSP4 signal as it is has difficulties in stabilizing circuits.

In contrast, this embodiment uses, for resetting, the vertical synchronizing signal $V_D$ occurring immediately after the edge of WSP4L. Therefore, after initial phases are matched with a predetermined timing signal, after a power supply is turned on, the VRESET signal is constantly tracked by a signal having the same phase. Therefore, a feedback circuit is not formed in a steady state. Consequently, this embodiment permits stable phase matching which is unaffected by a jitter component of the phase detected signal WSP.

According to the above construction, the third embodiment permits common use of a color field sequential illuminating means whose frame frequency differs from that of a monitor. This embodiment can easily generate standard TV signals whose frame frequency differs from that of the color field sequential illuminating means and imaging means, without causing, disadvantages such as out-of-synchronism and lead scan.

Figure 9:
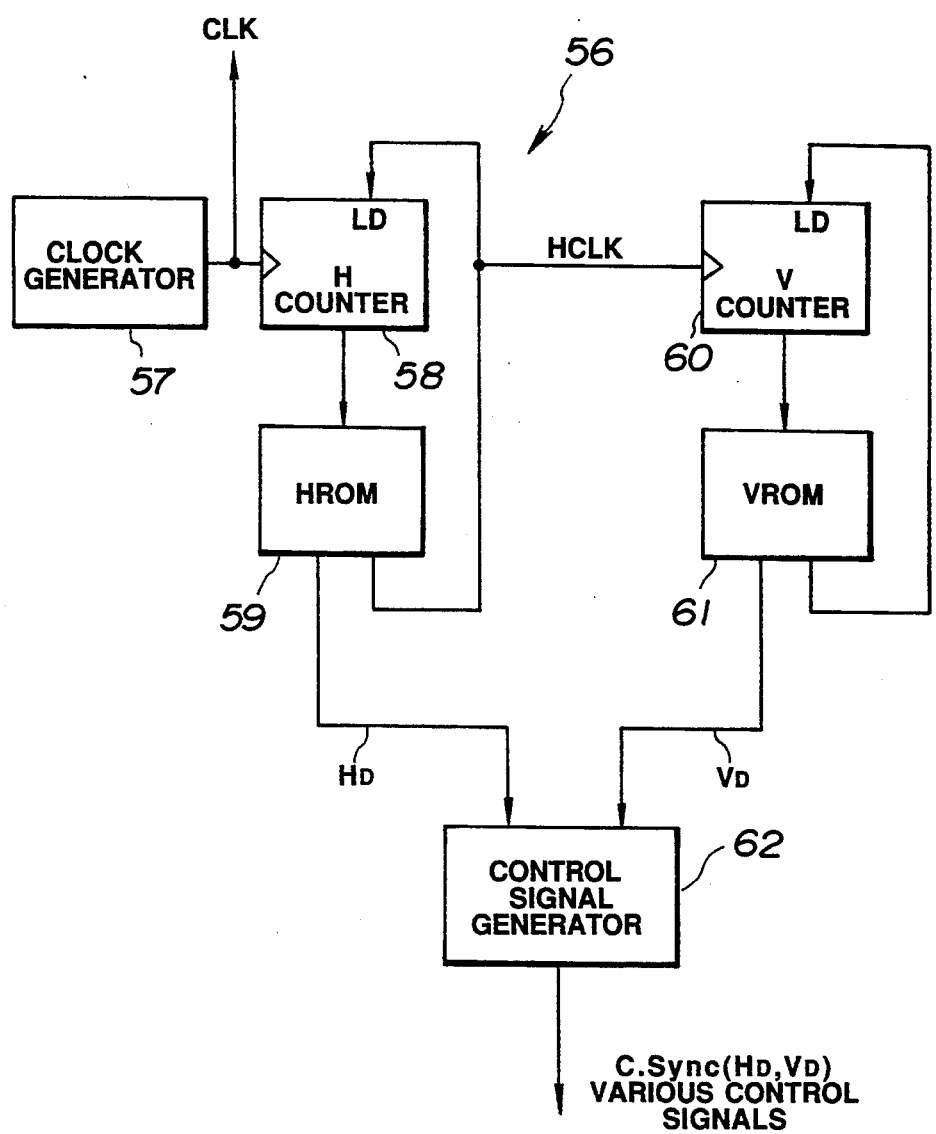
FIG. 9 is a block diagram of a second control circuit relating to the fourth embodiment.

FIG. 9 is a block diagram of a second control circuit according to the fourth embodiment of the present invention.

A second control circuit 56 according to the fourth embodiment comprises a clock generator 57 for generating a reference clock CLK, a horizontal counter (hereafter, abbreviated as H counter) 58, a horizontal ROM (hereafter, abbreviated as HROM) serving as a horizontal memory means, a vertical counter (hereafter, abbreviated as V counter) 60, a vertical ROM (hereafter, abbreviated as VROM) serving as a vertical memory means 61, and a control signal generating circuit 62.

The H counter 58 counts up a reference clock CLK sent from the clock generator 57, and outputs a count value as an address in the HROM 59. The H counter 58 is loaded according to the timing data pre-written in the HROM 59. Therefore, the H counter 58 can be operated as a counter for a specified period, for example, a horizontal period of a second standard TV system. Specifically, the data (timing) written in the HROM 59 varies depending on an address specified with the count and represents "high" for each horizontal period or "low" for the period other than horizontal period. Data corresponding to one horizontal period of the second standard TV system is sufficient for the HROM 59.

The data pre-written in the HROM 59 is read periodically and sent as a horizontal synchronizing signal of the second standard TV system to the control signal generating circuit 62.

The V counter 60 counts up a horizontal clock HCLK for loading, which is supplied from the HROM 59, and outputs a count value as an address in the VROM 61. The horizontal clock HCLK is also a signal having a horizontal period of the second standard TV system.

The V counter 60 is loaded (LD) according to the timing data pre-written in the VROM 61. Therefore, the V counter 60 also operates as a counter for a specified period. Specifically, the data (timing) written in the VROM 61 varies depending on an address specified with a count, and represents, for example, "high" for each vertical period of the second standard TV system and "low" for the period other than vertical period. Data corresponding to one vertical period of the second standard TV system is sufficient for the VROM 61.

The data pre-written in the VROM 61 is read periodically, and supplied as a vertical synchronizing signal of the second standard TV system to the control signal generating circuit 62.

The control signal generating circuit 62 synthesizes the horizontal synchronizing signal $H_D$ and vertical synchronizing signal $V_D$, which are read from the HROM 59 and VROM 61, to generate and output a synchronizing signal of the second standard TV system such as a composite synchronizing signal C.SYNC, a memory read control signal synchronous with the synchronizing signal, a D/A conversion control signal, and a timing control signal for the second signal processing circuit.

The other components, operation, and advantages are identical to those of the first embodiment. The description will, therefore, be omitted.

Figure 10:
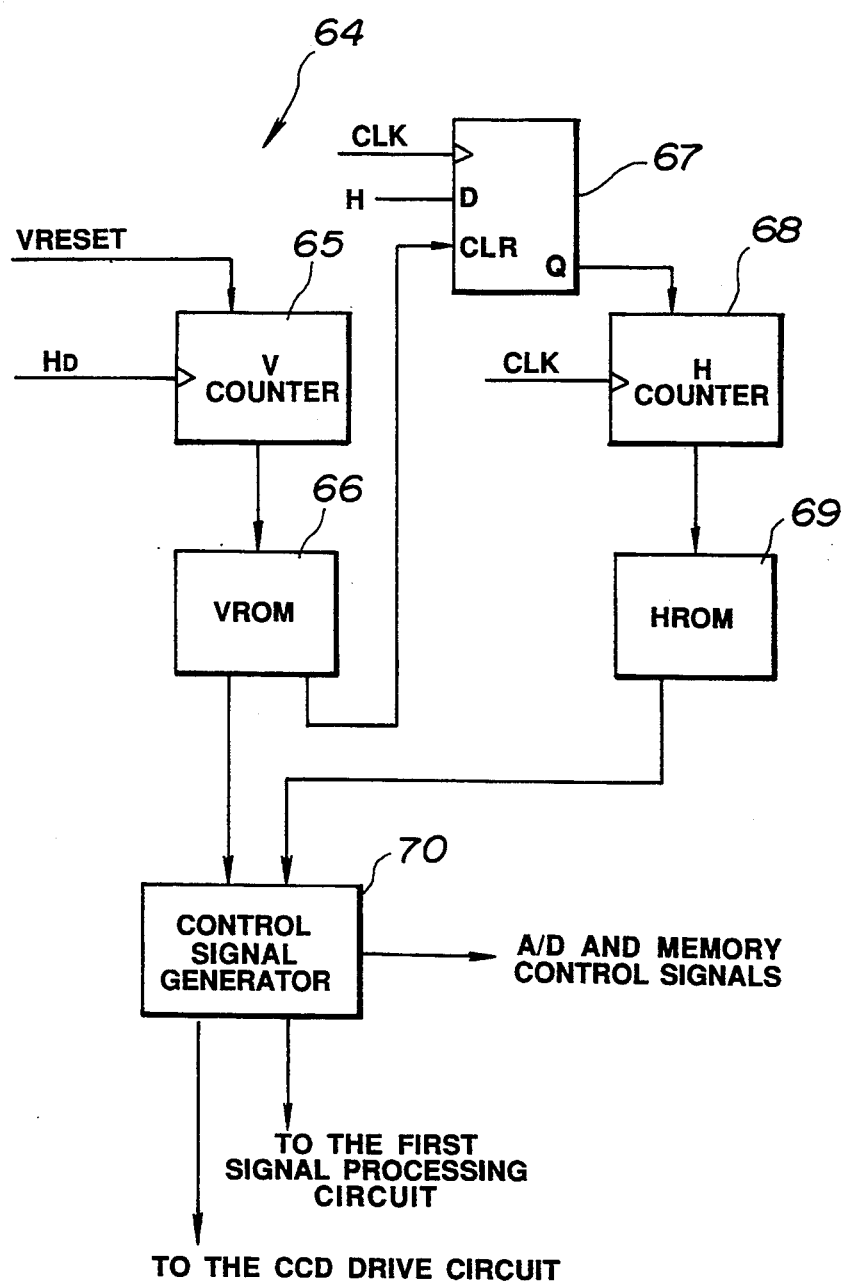
FIG. 10 is a block diagram of a first control circuit relating to the fifth embodiment.

FIG. 10 is a block diagram of a first control circuit relating to the fifth embodiment of the present invention.

As shown in FIG. 10, a first control circuit 64 comprises a V counter 65 for inputting a reset signal VRESET provided by a timing control circuit 50 shown in FIG. 7 and a horizontal synchronizing signal $H_D$ of a second standard TV system, a VROM 66 serving as a vertical memory means, a D flip-flop (hereafter, D-FF) circuit 67, an H counter 68, a HROM 69 serving as a horizontal memory means, and a control signal generating circuit 70.

With the construction of the V counter 65 and VROM 66, a signal is supplied at each vertical period. In other words, a vertical synchronizing signal is generated. The V counter 65 counts up a horizontal synchronizing signal $H_D$, and resets the count in response to a reset signal VRESET. The reset signal VRESET is generated when the synchronizing signals of a first standard TV system and a second standard TV system are put substantially in phase.

The count of the V counter 65 is placed as an address in the VROM 66. In the VROM 66, data "high" is written at a vertical period of the first standard TV system. Data corresponding to a repetition period of the reset signal VRESET is sufficient for the VROM 66. Alternatively, the VROM 66 may contain the data corresponding to an integral multiple of the repetition period.

Twelve vertical periods of the NTSC system correspond substantially to ten vertical periods of the PAL system. Assuming that the first standard TV system is NTSC and the second standard TV system is PAL, data corresponding to ten PAL vertical periods represents an entire NTSC synchronizing signal. That is to say, one period of the reset signal VRESET corresponds substantially to ten PAL vertical periods. A difference between a PAL period and an NTSC period is approximately 200 μs, which is negligible.

An output of the VROM 66 is fed to a clear terminal of the D-FF circuit 67. In the D-FF circuit 67, a data input terminal is pulled up to "high" and a clock terminal receives a reference clock CLK. An output terminal Q of the D-FF circuit 67 is connected to a reset terminal of the H counter 68.

The reference clock CLK may be the same as or different from that shown in FIG. 9. However, when the reference clock CLK is different from that shown in FIG. 9, the clocks must be locked in phase at the timing of a horizontal period.

The H counter 68 counts up the reference clock CLK, and resets the count in response to a Q output of the D-FF circuit 67. The count value of the H counter 68 is placed as an address in the HROM 69. Based on the input address value, by means of the pre-written data, the HROM 69 outputs a high-level signal for each horizontal period of the first standard TV system, and a low-level signal for the period other than horizontal period time. The HROM 69 contains the data corresponding to an integral multiple of a horizontal period.

The control signal generating circuit 70 uses a vertical synchronizing signal $V_H$ read from the VROM 66 and a horizontal synchronizing signal $H_D$ read from the HROM 69 to generate a composite synchronizing signal C.SYNC, a CCD driving signal, respective control signals for controlling operations of the first signal processing circuit, A/D converters, and writing in memory or the like.

In this embodiment, a field sequential light source apparatus for an endoscope having an imaging frame frequency conformable to, for example, the NTSC system is used for imaging, and video signals conformable to, for example, the PAL system are supplied. As long as at least the imaging frame is conformable to the NTSC system, even if signals are not in phase perfectly, the present invention achieves objects thereof. Therefore, the HROM 69 stores data in which horizontal timing of imaging is set so that all the necessary pixels of a CCD 25 can be read during an interception period (for example, an cycle of 16.7 ms and a width of 8.2 ms) for each one-field NTSC period. Assuming that the reference clock CLK has a frequency of 16.09375 MHz, the CCD driving frequency is 8.05 MHz, and the number of pixels of the CCD is 200 by 200, if CCD read is driven at the rate of three lines per two PAL horizontal periods, the data of all the pixels of the CCD can be read during the interception period. Therefore, in the aforesaid embodiment, the data corresponding to two PAL horizontal periods are placed in the HROM 69. The control signal generating circuit 70 drives CCD read for three lines during two horizontal periods, and generates control signals for controlling signal processing.

In the foregoing construction, the VRESET signal representing that the phases of the first and second standard TV systems are matching is fed by the timing control circuit 50. With the VRESET signal, the V counter 65 is reset. The V counter 65 counts up a horizontal synchronizing signal $H_D$ fed by, for example, a second control circuit 56 shown in FIG. 9, and outputs the count value as an address value of the VROM 66. According to the input address value, the data pre-written in the VROM 66 is read and supplied as a vertical synchronizing signal to the control signal generating circuit 70.

An output of the VROM 66 is fed to the D-FF circuit 67 that has a clear terminal, whereby the edge of the output is sampled. With the sampled output, the H counter 68 is reset.

The H counter 68 outputs a count of reference clocks CLK fed by a clock generator, which is not shown, as an address value of the HROM 69. According to the input address value, the pre-written data is read from the HROM 69, and supplied as a horizontal synchronizing signal $H_D$ to the control signal generating circuit 70. The control signal generating circuit 70 uses the synchronizing signals $H_D$ and $V_D$ to generate and output a CCD driving signal, a timing control signal for the first signal processing circuit, control signals for controlling the operations of the A/D converters, and control signals for controlling writing in memories.

Figure 11:
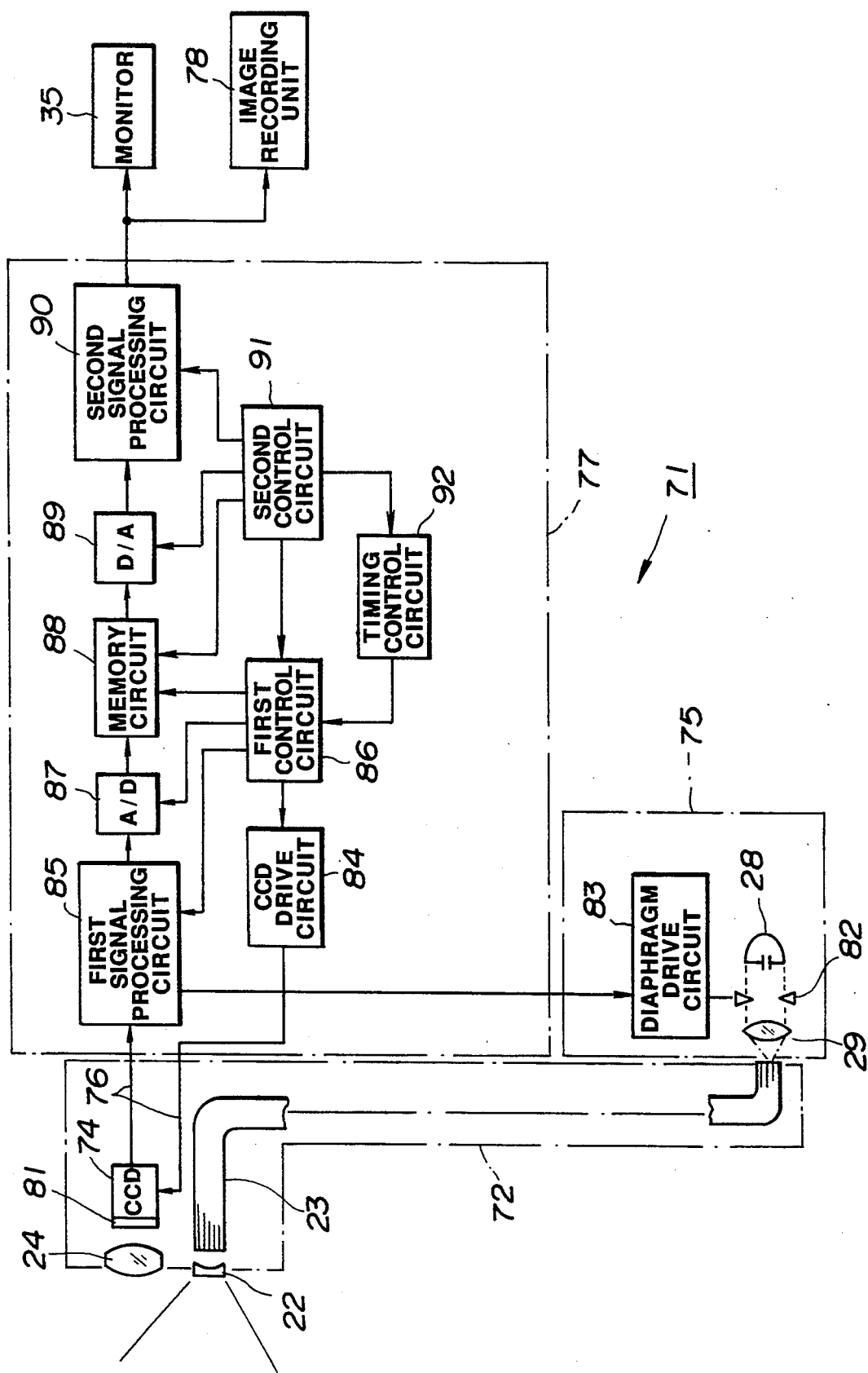
FIG. 11 is a block diagram of an electronic endoscope system relating to the sixth embodiment.

Next, the sixth embodiment will be described. An electronic endoscope system of the sixth embodiment shown in FIG. 11 is an example of a simultaneous imaging type system in which the present invention is implemented. The components identical to those shown in FIG. 2 are assigned the same numerals. The description will be omitted.

An electronic endoscope system 71 of this embodiment includes an electronic endoscope 72 in which a CCD 74 serving as an imaging means is installed at the distal end of an insertion section, and a light source apparatus 75 for generating white illumination light.

The electronic endoscope system 71 includes a signal processing unit 77 that drives the CCD 74 via a signal line 76 inserted through the endoscope 72, performs given processing on read signals, and outputs TV signals conformable to the standard TV system adopted in a monitor 35 connected externally or in an image recording unit 78.

In the electronic endoscope 72, as shown in FIG. 12a, a color separation filter array 79 is attached to the imaging plane. The color separation filter array 79 consists of multiple color mosaic filters of, for example, yellow (Ye), cyan (Cy), magenta (Mg), and green (G).

A YAG cutoff filter 80 for cutting off YAG laser beam components and a crystal filter 81 for cutting off infrared light are arranged in that order from the distal end between an objective optical system 24 and the color separation filter array 79 of the CCD 74. That is to say, an imaging system is formed to pass visible light components alone.

In a light source apparatus 75, a diaphragm 82 is placed between a lamp 28 and a condenser lens 29. The diaphragm 82 adjusts a quantity of white light coming from the lamp 28 and entering a light guide 23. The aperture size of the diaphragm 82 is controlled by a diaphragm drive circuit 83.

An optical image of a subject illuminated with illumination light from the light source apparatus 75 is formed on the imaging plane of the CCD 74. At this time, the optical image is separated in colors by the color separation filter array 79 attached to the front of the CCD 74, converted photoelectrically by the CCD 74, then read as electric signals under the control of the CCD driving circuit 84.

The CCD driving circuit 84 drives the CCD 74 for imaging at a first frame frequency (for example, 29.97 frames/sec that is conformable to the NTSC system) according to an output of a first control circuit which will be described later.

The CCD 74 is driven by the CCD driving circuit 84 of the signal processing unit 77, whereby data is read from the CCD 74. Then, the CCD 74 generates dot sequential image signals at a first frame frequency, and outputs the signals to a first signal processing circuit 85.

The first signal processing circuit 85 performs a variety of signal processing on the image signals sent from the CCD 47 under the control of a first control circuit 86. The variety of signal processing include, for example, clamping, automatic gain control (AGC), knee point correction, clipping, gamma correction, filtering, color separation, automatic light control detection, and white balance control. The first signal processing circuit 85 supplies the signals, which have undergone the given processing, to memory circuits 88 via A/D converters 87.

Figure 12:
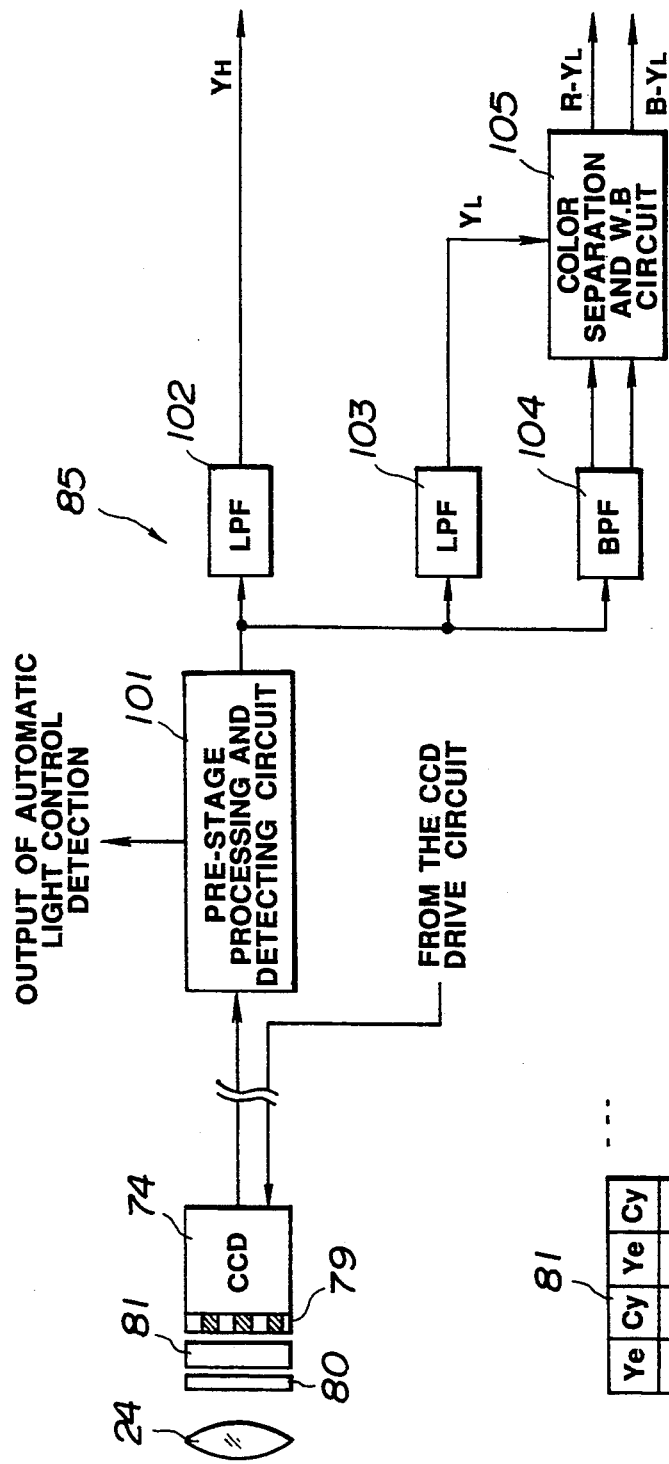
FIG. 12 is a block diagram relating to an example of a first signal processing circuit shown in FIG. 11.

FIG. 12 is a block diagram showing an example of a first signal processing circuit 85. The first signal processing circuit 85 includes a pre-stage processing-/detecting circuit 101 for performing various signal processing; such as, gamma correction, AGC, and automatic light control detection. An output resulting from detection for automatic light control is supplied from the pre-stage processing/detecting circuit 101 to the diaphragm drive circuit 83. The diaphragm drive circuit 83 optimally controls the aperture size of the diaphragm 82 according to the output resulting from detection for automatic light control.

The pre-stage processing/detecting circuit 101 outputs image signals, which have undergone the various signal processing, to low-pass filters (hereafter, abbreviated LPF) 102 and 103, and a bandpass filter (hereafter, BPF) 104. The LPFs 102 and 103 performs band-limitation to the image signals to obtain a broadband luminance signal $Y_H$ and a narrow-band luminance signal $Y_L$ respectively.

An output of the BPF 104 is fed to a color separation/white balance circuit 105. The color separation/white balance circuit 105 uses the outputs of the BPF 104 and LPF 103 to perform given operation, whereby white balance is attained and color difference signals $R-Y_L$ and $B-Y_L$ are produced.

A/D converters 87 convert outputs of the first signal processing circuit 85 into digital signals. For example, when the first signal processing circuit 85 has construction shown in FIG. 12, the A/D converters 87 provides a digital luminance signal Y, and digital color difference signals $R-Y$ and $B-Y$.

Memory circuits 88 contains the digital luminance signal Y, and the digital color difference signals $R-Y$ and $B-Y$, which are supplied by the A/D converters 87. Respective data read from the memory circuits 88 are converted into analog signals by D/A converters 89, and fed to a second signal processing circuit 90.

The memory circuits 88 are read simultaneously under the control of the second control means 91; that is, at timing of a second frame frequency (for example 25 frames/see that is conformable to the PAL system). The D/A converters 89 perform conversion at timing of the second frame frequency.

The second signal processing circuit 90 performs various signal processing on the luminance and color difference signals, which are made concurrent synchronously with, for example, PAL TV signals, based on a timing signal from the second control circuit 91. The various processing performed by the second signal processing circuit 90 include, for example, clamping, masking, matrixing, contour correction, clipping, and PAL encoding. After completing given signal processing, the second signal processing circuit 90 outputs PAL TV signals or other TV signals conformable to the TV system of the monitor 35 to the monitor 35. Alternatively, the output of the second signal processing circuit 90 is supplied to a PAL VTR or other an image recording unit 78.

The second control circuit 91 generates a TV synchronizing signal with a second frame frequency, makes the above control, and outputs the synchronizing signal to the first control circuit 86.

On the other hand, the first control circuit 86 uses the synchronizing signal from the second control circuit 91 to generate a synchronizing signal with a first frame frequency and signals for the control operations described below. Specifically, the first control circuit 86 controls the timing of signal processing by the first signal processing circuit 85, the timing of conversion by the A/D converters 87, and the writing in the memory circuits 88. These control operations are performed at timing synchronized with thee first frame frequency.

A timing control circuit 92 is installed to match the frame phases of the first and second control circuits 86 and 91. The timing control circuit 92 generates a signal for resetting the frame phase of the first control circuit 86 using a predetermined timing signal sent from the second control circuit 91.

In this embodiment, a phase specified in the first control circuit 86 is reset at each cycle of a frequency equivalent to a maximum common measure between the first and second frame frequencies. Assuming that the first and second frame frequencies conform, for example, to the NTSC and PAL systems respectively, a phase is reset at every five frames (in unit of 5 Hz). Herein, five frames make up a frequency equivalent to the maximum common measure.

The first frame frequency must not be conformable to a first standard TV system, but must be an integral multiple of the frame frequency of a second standard TV system.

This embodiment can easily generate TV signals with a frame frequency, which is different from a frame frequency adopted in an imaging system, without causing disadvantages such as out-of-synchronism and lead scan. This embodiment can supply stable TV signals to a monitor, an image recording unit, or the like.

In this embodiment, multiple electronic endoscopes which output signals conformable to different TV systems can share substantially all operations; such as, generating a CCD drive signal, driving a CCD, and handling a CCD read signal. Thus, excellent development efficiency ensues. Moreover, this embodiment can be easily realized with ICs, facilitating mass production potentiality.

The other components identical to those of the first embodiment are assigned the same numerals. The components and the operation identical to that of the first embodiment will not be described.

Figure 13:
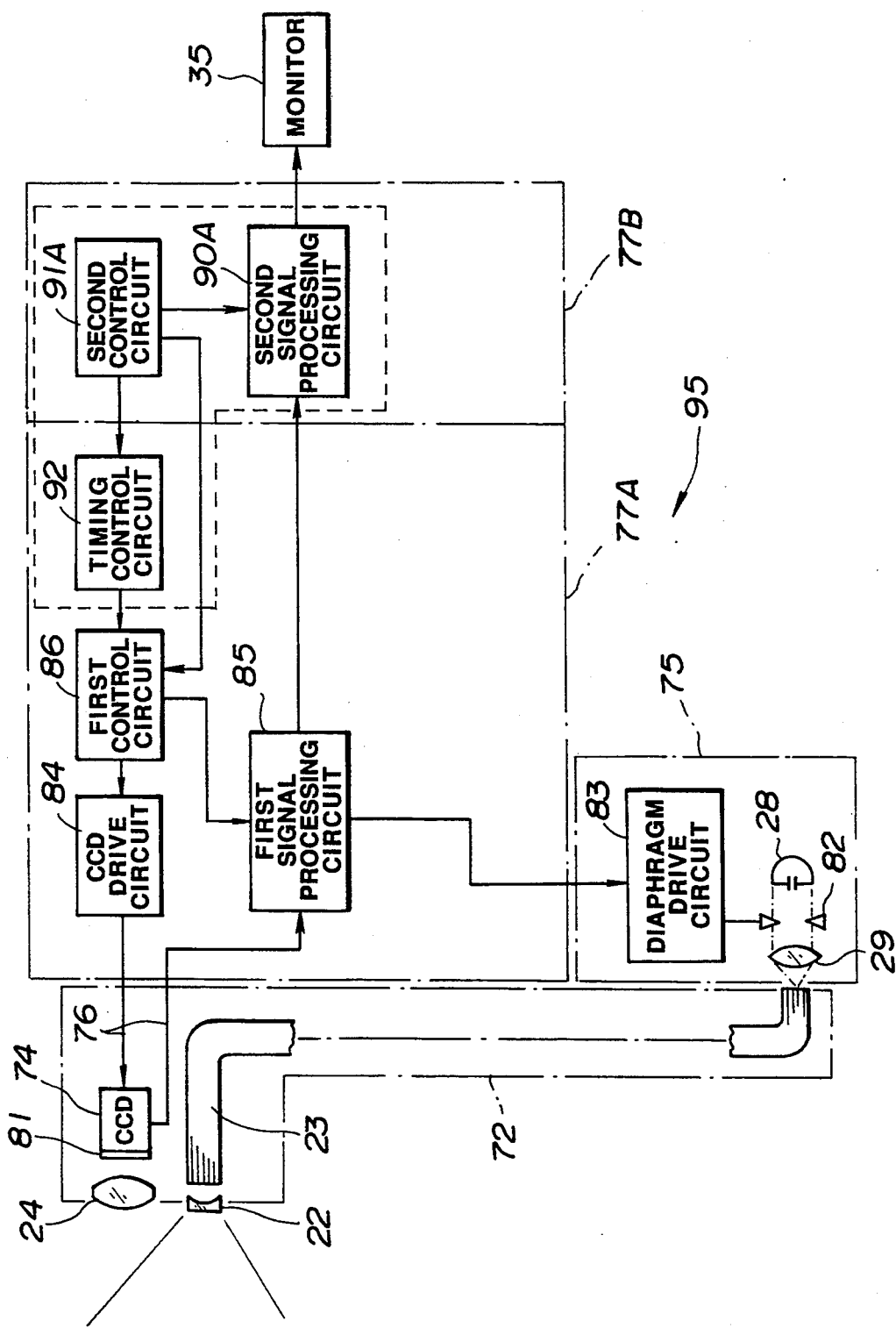
FIG. 13 is a block diagram of an electronic endoscope system relating to the seventh embodiment.

FIG. 13 is a block diagram of an electronic endoscope system relating to the seventh embodiment of the present invention.

A system of this embodiment is, similarly to the sixth embodiment, materialized as a simultaneous imaging type system. In the seventh embodiment, the components identical to those in the sixth embodiment are assigned the same numerals. The components, and the operation identical to that of the sixth embodiment will not be described.

An endoscope system 95 of the seventh embodiment includes a signal processing unit 77A in which a circuit group included in the sixth embodiment shown in FIG. 11 for processing signals at a first frame frequency are incorporated. The signal processing unit 77A comprises a CCD drive circuit 84, a first control circuit 86, a first signal processing circuit 85, and a timing control circuit 92 for resetting a frame phase.

The endoscope system 95 includes a signal converting unit 77B made up of a second control circuit 91A and a second signal processing circuit 90A that adopt a second frame frequency. The signal converting unit 77B is detachable from the signal processing unit 77A. In other words, the second control circuit 91A and second signal processing circuit 90A are detachable from the signal processing unit 77.

In the seventh embodiment, the second signal processing circuit 90A includes A/D converters, memory circuits 88, and D/A converters 89, in addition to a second signal processing circuit 90 included in the embodiment shown in FIG. 11. The second control circuit 91A not only functions similarly to a second control circuit 91 shown in FIG. 11 but also controls memory write. The other circuit operations are identical to those of the sixth embodiment.

Owing to the foregoing construction, the present embodiment can be connected to a monitor, an image recording unit, or a hard copy unit such as a video printer, which operates according to a different TV system, merely by replacing a signal converting unit. That is to say, while an endoscope, a light source apparatus, and a signal processing unit are used in common, only when signal converting units of different TV systems are changed, multiple monitors with different TV systems can be connected. Instead of the monitors, this embodiment can also be connected to a unit that receives signals of a different TV system and which is constructed as an existing system, when a signal converting unit is placed between them.

In an electronic endoscope system shown in FIG. 13, a signal processing unit may include a timing control circuit (made using, for example, ICs) as indicated with a dashed line in FIG. 13.

The other components, operation, and advantages are identical to those of the six embodiment. The description will, therefore, be omitted.

In the sixth or seventh embodiment, a second control circuit 91 or 91A may be formed similarly to a second control circuit 56 shown in FIG. 9. In the sixth or seventh embodiment, a first control circuit 86 may be formed similarly to a first control circuit 64 shown in FIG. 10.

Figure 14:
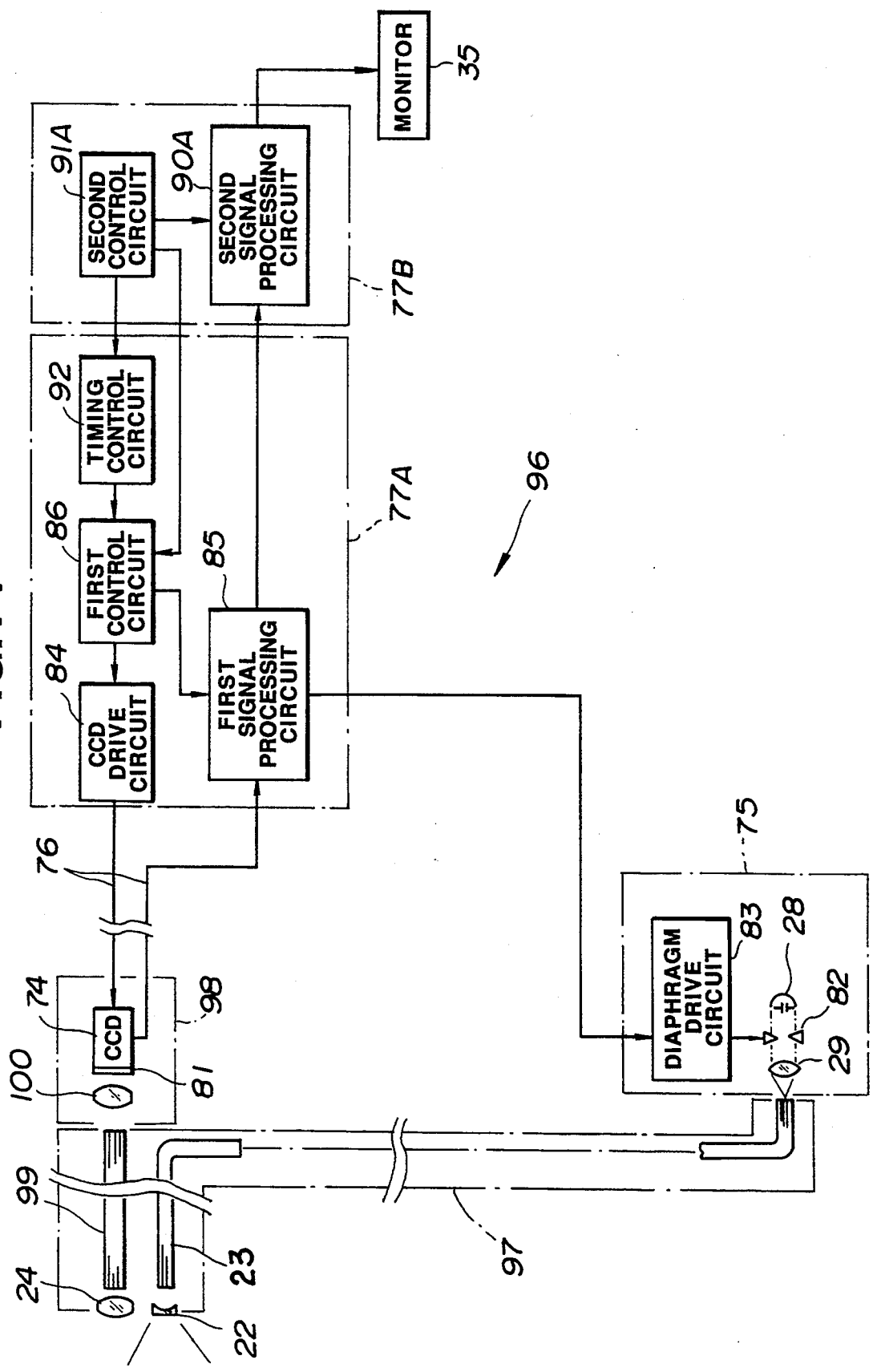
FIG. 14 is a block diagram of an electronic endoscope system relating to a variant of the seventh embodiment.

FIG. 14 is a block diagram of an electronic endoscope system relating to a variant of the seventh embodiment.

An electronic endoscope system 96 of this variant includes an external endoscopic TV camera 98 that is detachable from an optical fiber endoscope 97. The other components identical to those of the seventh embodiment are assigned the same numerals. The components and the operation identical to that of the seventh embodiment will not be described.

In the optical fiber endoscope 97, image guide fibers 99 are attached to the rear end of an objective optical system 24. The image guide fibers 99 are extending from the distal end of the endoscope 97 to an eyepiece unit. The external TV camera 98 forms an optical image transmitted through the image guide fibers 99 on the imaging plane of a CCD 98 via an image formation lens 100.

The other components, operation, and advantages are identical to those of the seventh embodiment. The description will be omitted.

In the aforesaid embodiments and variant, a first control circuit is reset by a timing control circuit using a second control circuit as a reference. The roles of the first and second control circuits may be reverse.

In the aforesaid embodiments, a first standard TV system is NTSC, and a second standard TV system is PAL. The first and second standard TV systems may be reverse. Alternatively, SECAM may be adopted instead of either of these systems.

When a liquid crystal light valve or other diaphragm is installed in a light source apparatus, a tone variation in an observation image resulting from a change in the area of an aperture of the diaphragm that is caused by near observation must be prevented.

In an endoscope having an automatic diaphragm mechanism in front of a CCD, a color correction filter for compensating for a change in spectral transmission characteristic resulting from automatic diaphragmatic operation is placed on an optical axis between a lamp and an incident end of a light guide in a light source apparatus for controlling drive of the automatic diaphragm mechanism. Based on an output signal of a photomerry or range finding means installed in front of the automatic diaphragm mechanism, the color correction filter is advanced to or withdrawn from an optical path of illumination light. Moreover, an aperture diameter determining means is incorporated to indicate an aperture diameter to a drive control means for the automatic diaphragm mechanism in the light source apparatus.

In the foregoing construction, the color correction filter advances to or withdraws from the optical path of illumination light in the light source apparatus synchronously with automatic diaphragmatic operation. This prevents a tone variation from occurring in an observation image as a result of a change in the area of the aperture of the diaphragm.

In this embodiment, it will be apparent that a wide range of embodiments can be constructed on the basis of the spirit of the present invention. The invention is limited to the appended claims but not restricted to any specific embodiment.

What is claimed is:

1. An electronic endoscope system comprising:
   a color field sequential illuminating means for emitting, at a frame frequency of a first standard TV system, color field sequential illumination light for sequentially illuminating a subject with a plurality of light rays of different color components;
   an imaging means for imaging said subject under illumination light of said color field sequential illuminating means;
   a signal generating means for receiving color field sequential image signals acquired by said imaging means, and generating video signals of a second standard TV system having a frame frequency which is approximately n/m-fold of that of said first standard TV system where n and m are natural numbers and n is unequal to m;
   a first control means for generating a pseudo imaging sync signal having a frequency which is approximately m/n-fold of said frame frequency of said second standard TV system in order to control said field sequential illuminating means, and controlling said imaging means so that color field sequential imaging will be performed at a frequency which is m/n-fold of said frame frequency of said second standard TV system;
   a second control means for generating a synchronizing signal of said second standard TV system;
   a detecting means for detecting at least a repetition period of said color field sequential illuminating means;
   a timing control means for comparing at least a period detected by said detecting means with that of said synchronizing signal generated by said second control means, and phasing a signal generated by said first control means, based on the result of said comparing; and
   a color field sequential illumination control means for controlling the phase of color field sequential illumination repeated in said color field sequential illuminating means so as to be synchronized with said pseudo imaging sync signal input from said first control means.

2. An electronic endoscope system comprising:
   a color field sequential illuminating means for emitting, at a frame frequency of a first standard TV system, color field sequential illumination light for sequentially illuminating a subject with a plurality of light rays of different color components;
   an imaging means for imaging said subject under illumination light of said color field sequential illuminating means;
   a signal generating means for receiving color field sequential image signals acquired by said imaging means, and generating video signals of a second standard TV system having a frame frequency which is approximately n/m-fold of that of said first standard TV system, where n and m are natural numbers, and n is unequal to m;
   a first control means for generating a pseudo imaging sync signal having a frequency which is approximately m/n-fold of said frame frequency of said second standard TV system in order to control said field sequential illuminating means, and controlling said imaging means so that color field sequential imaging will be performed at a frequency which is m/n-fold of said frame frequency of said second standard TV system;
   a second control means for generating a synchronizing signal of said second standard TV system;
   a detecting means for detecting at least a phase of said color field sequential illuminating means;
   a timing control means for comparing at least a phase detected by said detecting means with that of said synchronizing signal generated by said second control means, and phasing a signal generated by said first control means, based on the result of said comparing; and
   a color field sequential illumination control means for controlling the phase of the color field sequential illuminating means so as to be synchronized with said pseudo imaging sync signal input from said first control means.

3. An electronic endoscope system according to claim 1 or 2, wherein said timing control means periodically phases a signal generated by said first control means.

4. An electronic endoscope system according to claim 1 or 2, wherein after a power supply is turned on, when color field sequential illumination iterated by said color field sequential illuminating means comes to have substantially a specified period, said timing control means phases a signal generated by said first control means.

5. An electronic endoscope system according to claim 1 or 2, wherein said first standard TV system is any of NTSC, PAL, and SECAM; and
said second standard TV system is a system different from said first standard TV system and is any of NTSC, PAL, and SECAM.

6. An electronic endoscope system according to claim 1 or 2, wherein said first control means uses at least either a vertical synchronizing signal or a horizontal synchronizing signal, which is output by said second control means, to generate said pseudo imaging sync signal, and controls said color field sequential illuminating means and said imaging means according to said first standard TV system.

7. An electronic endoscope system according to claim 1 or 2, wherein said signal processing means includes first converting means for converting color field sequential image signals acquired by said imaging means from the analog form to the digital form, storing means for storing the outputs of said first converting means written thereto, and second converting means for converting data read from said storing means from the digital form to the analog form;
said first control means controls the timing of reading color field sequential image signals from said imaging means, the timing of conversion performed by said first converting means, and the timing of writing in said storing means; and
said second control means controls the timing of reading from said storing means, and the timing of conversion performed by said second converting means.

8. An electronic endoscope system according to claim 1 or 2, wherein said second control means includes:
a reference clock signal producing means for generating a reference clock signal;
a horizontal counter that counts up pulses of said reference clock signal and operates as a counter for a specified period in response to a horizontal load signal;
a horizontal memory means for storing data for outputting a horizontal synchronizing signal only when the count of said horizontal counter, which has been input as an address, indicating a set value, and outputting a horizontal load signal for loading said horizontal counter; a vertical counter for counting up a horizontal load signal provided by said horizontal memory means and operating as a counter for a specified period in response to a vertical load signal; and
a vertical memory means for storing data for outputting a vertical synchronizing signal only when the count of said vertical counter, which has been input to an address, indicates a set value, and outputting a vertical load signal for loading said vertical counter.

9. An electronic endoscope system according to claim 1 or 2, wherein said first control means includes:
a vertical counter for counting up a synchronizing signal provided by a second control means and resetting said vertical counter in response to a phasing signal output by said timing control means;
a vertical memory means for storing data for outputting a vertical synchronizing signal only when the count of said vertical counter, which has been input as an address, indicates a set value;
a horizontal counter for counting up pulses of a reference clock signal and resetting the count of said reference clock signal when a count input as an address in said vertical memory means indicates said set value; and
a horizontal memory means for storing data for outputting a horizontal synchronizing signal only when the count of said horizontal counter, which has been input as an address, indicates a predetermined value.

10. An electronic endoscope system according to claim 1 or 2, wherein said timing control means includes:
a frequency dividing means for dividing the frequency of a signal detected by said detecting means in conformity with a frequency at which a frequency of a synchronizing signal of said first standard TV system, a frequency of a synchronizing signal of said second standard TV system, and a frequency of color frames repeated in said color field sequential illuminating means match substantially;
an edge sampling means for detecting an edge of a signal, the frequency of which is divided by said frequency dividing means, in response to a synchronizing signal of said second standard TV system; and
a gate means for outputting a reset signal for phasing when a synchronizing signal of said second standard TV system and an output of said edge sampling means substantially lock onto each other.

11. An electronic endoscope system according to claim 4, wherein said timing control means includes a period detecting means for detecting that the period of color field sequential illumination repeated in said color field sequential illuminating means has become a specified period, and phases a signal, which is generated by said first control means, according to the result of said comparing, when said period detecting means detects that the specified period has been attained.

12. An electronic endoscope system according to claim 10, wherein said edge sampling means generates a synchronous period signal having a width that ranges from the timing of a synchronizing signal of said second standard TV system occurring at the trailing edge of a signal whose frequency is divided by said frequency dividing means to the timing of the subsequent next synchronizing signal; and
said gate means outputs said reset signal for phasing when a synchronous period signal provided by said edge sampling means and a synchronizing signal of said second standard TV system lock onto each other.

13. An electronic endoscope system according to claim 10, wherein a synchronizing signal of said second standard TV system, which is input to said edge sampling means, is a vertical synchronizing signal.

14. An electronic endoscope system according to claim 12, wherein said timing control means includes a specified period detecting means that uses a synchronizing signal of said second standard TV system to detect that the period of a synchronous period signal provided by said edge sampling means is within a specified period; and
said gate means outputs a reset signal for phasing when a signal representing that the period of a synchronous time signal is within a specified period, which has been detected by said period detecting means, a synchronous period signal provided by said edge sampling means, and a synchronizing signal of said second standard TV system lock onto one another.

15. An electronic endoscope system according to claim 14, wherein said specified period detecting means uses a horizontal synchronizing signal generated by said second control means to detect whether or not the period of a synchronous period signal provided by said edge sampling means is within a specified period.

16. An electronic endoscope system according to claim 1 or 2, wherein said timing control means includes:

a frequency dividing means for dividing the frequency of a signal detected by said detecting means in conformity with a frequency at which a frequency of a synchronizing signal of said first standard TV system, a frequency of a synchronizing signal of said second standard TV system, and a frequency which is half a frequency of color frames repeated in said color field sequential illuminating means match substantially;

an edge sampling means for detecting an edge of a signal, frequency of which is divided by said frequency dividing means, in response to a synchronizing signal of said second standard TV system; and a gate means for outputting a reset signal for phasing when a synchronizing signal of said second standard TV system and an output of said edge sampling means substantially lock onto each other.

* * * * *